United States Patent [19]
Weiss et al.

[11] Patent Number: 5,097,950
[45] Date of Patent: Mar. 24, 1992

[54] SYSTEM FOR THE DISPOSAL OF MEDICAL WASTE

[75] Inventors: Mark E. Weiss; Eric L. Steiner, both of Denver; Jeffrey T. Samson, Boulder, all of Colo.

[73] Assignee: On-Gard Systems, Inc., Denver, Colo.

[21] Appl. No.: 515,204

[22] Filed: Apr. 27, 1990

[51] Int. Cl.⁵ .............................. B65D 85/20
[52] U.S. Cl. ............................ 206/366; 206/370; 220/404; 220/908
[58] Field of Search ............... 206/363-370, 206/554, 380, 438; 220/404, 908; 215/31

[56] References Cited

U.S. PATENT DOCUMENTS

| | | | |
|---|---|---|---|
| 118,163 | 8/1871 | Spalding | 215/31 |
| 755,085 | 3/1904 | Viano | |
| 800,401 | 9/1905 | Rounds | 215/31 |
| 2,080,144 | 5/1937 | Lufkin | 215/31 |
| 2,430,155 | 11/1947 | Buttery | 226/59 |
| 2,725,141 | 11/1955 | Latvala et al. | 206/554 |
| 3,309,160 | 3/1967 | Lewis | 220/909 |
| 3,843,041 | 10/1974 | Oliverius | 229/62 |
| 3,856,173 | 12/1974 | Deane et al. | 220/909 |
| 4,066,167 | 1/1978 | Hanna et al. | 383/62 |
| 4,077,562 | 3/1978 | Ballin | 383/62 |
| 4,182,448 | 1/1980 | Huck et al. | 206/380 |
| 4,315,592 | 2/1982 | Smith | 206/366 |
| 4,318,473 | 3/1982 | Sandel | 206/370 |
| 4,373,629 | 2/1983 | Ulin et al. | 206/350 |
| 4,383,530 | 5/1983 | Bruno | 604/274 |
| 4,452,358 | 6/1984 | Simpson | 206/366 |
| 4,466,538 | 8/1984 | Gianni | 206/370 |
| 4,485,855 | 12/1984 | Dillingham | 141/316 |
| 4,520,926 | 6/1985 | Nelson | 206/366 |
| 4,576,281 | 3/1986 | Kirksey | 206/366 |
| 4,580,688 | 4/1986 | Harris et al. | 206/366 |
| 4,600,112 | 7/1986 | Shillington et al. | 215/274 |
| 4,662,516 | 5/1987 | Baker, Sr. et al. | 206/366 |
| 4,722,472 | 2/1988 | Bruno | 229/128 |
| 4,736,844 | 4/1988 | Scott et al. | 206/370 |
| 4,801,013 | 1/1989 | Bruno | 206/366 |
| 4,804,090 | 2/1989 | Schuh et al. | 206/366 |
| 4,807,344 | 2/1989 | Kelson et al. | 29/240 |
| 4,809,850 | 3/1989 | Laible et al. | 206/366 |
| 4,826,073 | 5/1989 | Bruno | 229/128 |
| 4,828,107 | 5/1989 | Spencer | 206/366 |
| 4,842,138 | 6/1989 | Sandel et al. | 206/370 |
| 4,863,052 | 9/1989 | Lambert | 206/366 |
| 4,869,366 | 9/1989 | Bruno | 206/370 |
| 4,874,103 | 10/1989 | Ouisenberry et al. | 206/366 |
| 4,886,164 | 12/1989 | Stein | 206/366 |
| 4,911,294 | 3/1990 | Russo et al. | 206/366 |
| 4,917,263 | 4/1990 | Korb | 220/901 |
| 4,948,004 | 8/1990 | Chich | 220/909 |

*Primary Examiner*—Jimmy G. Foster
*Attorney, Agent, or Firm*—Sheridan, Ross & McIntosh

[57] ABSTRACT

A system for the disposal of medical waste comprises a sharps container (12) and a nonsharps container (14). The sharps container (12) is interconnected to the nonsharps container (14) for convenience. The sharps container (12) has an open end (18) with a semitortuous path therethrough which helps retain sharps within the sharps container (12). The nonsharps container (14) may also include an attachment holder (16 or 17) which is engaged thereon. A header (20) is positioned in an open end (22) of the nonsharps container (14). Medical nonsharps are disposed of by depositing them within the nonsharps container (14) through the header (20).

42 Claims, 5 Drawing Sheets

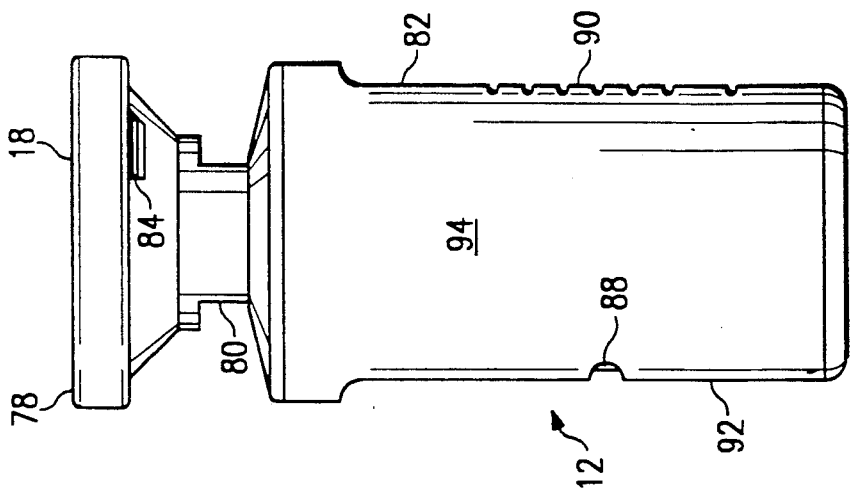
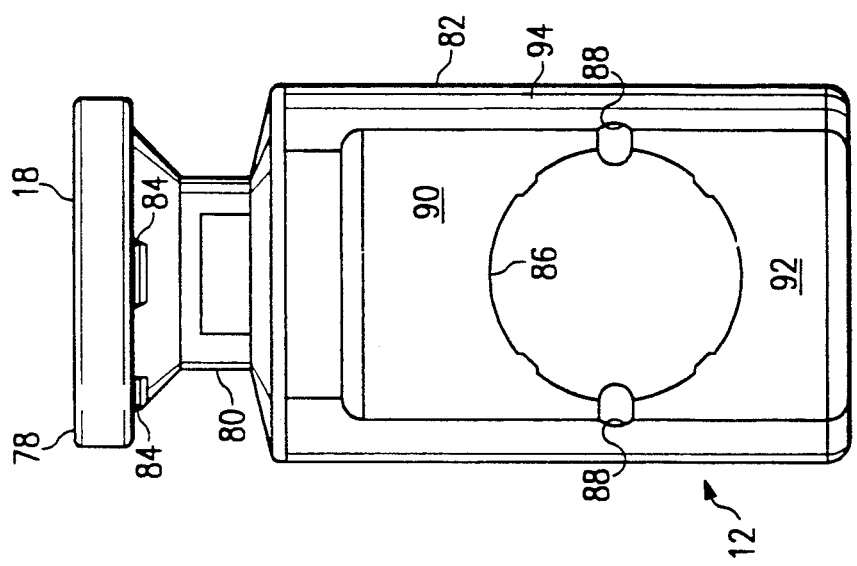
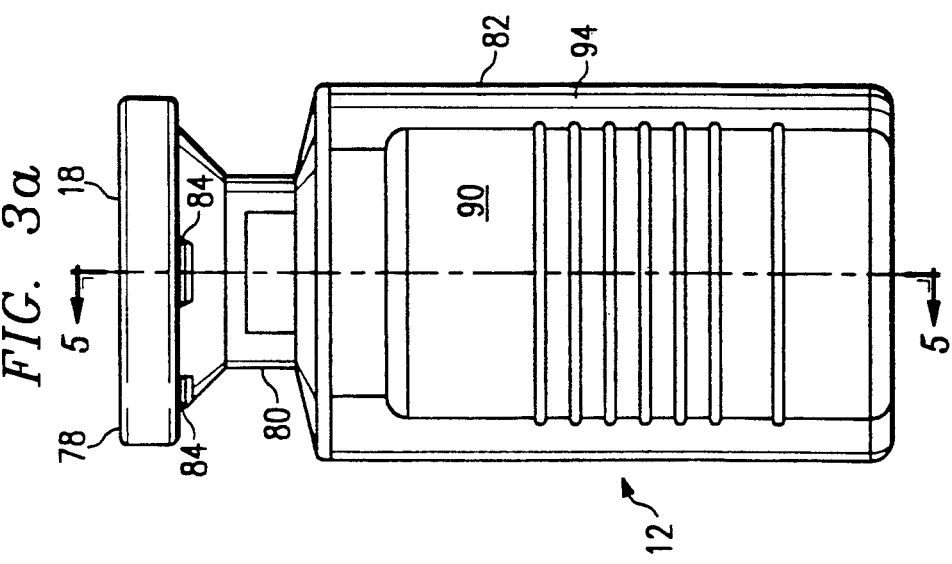

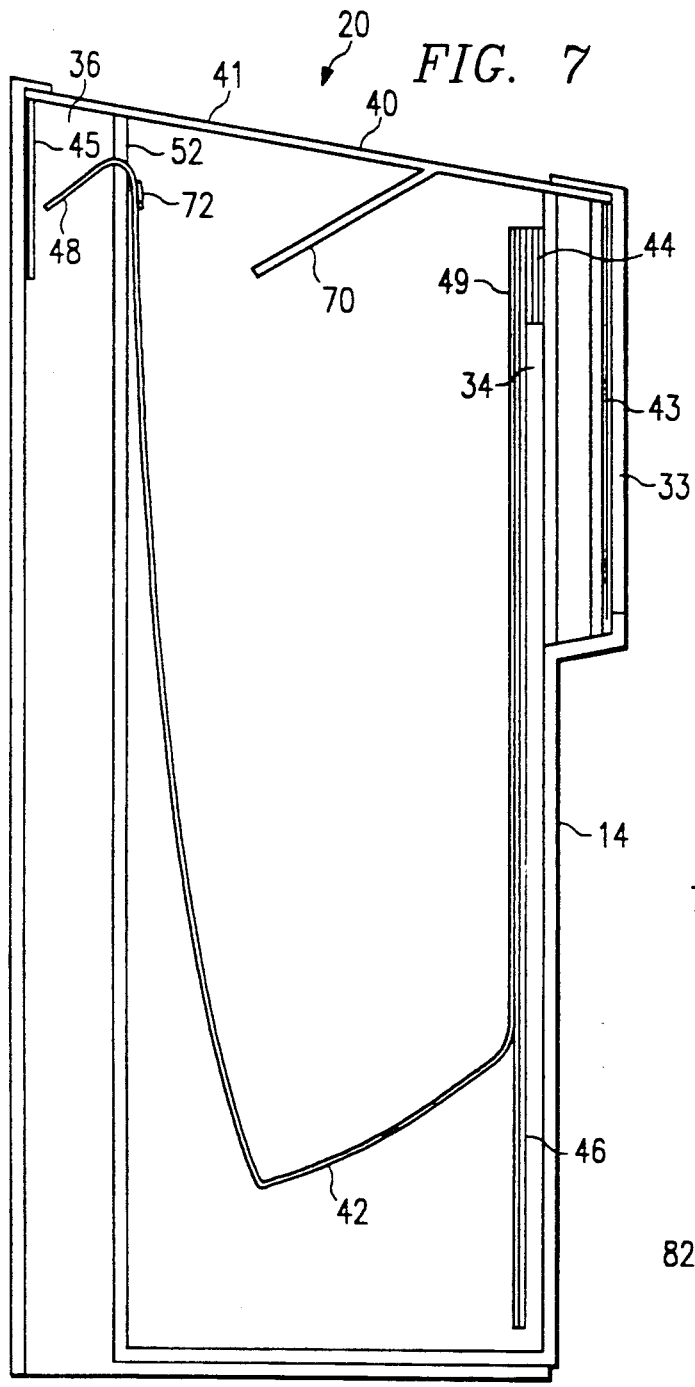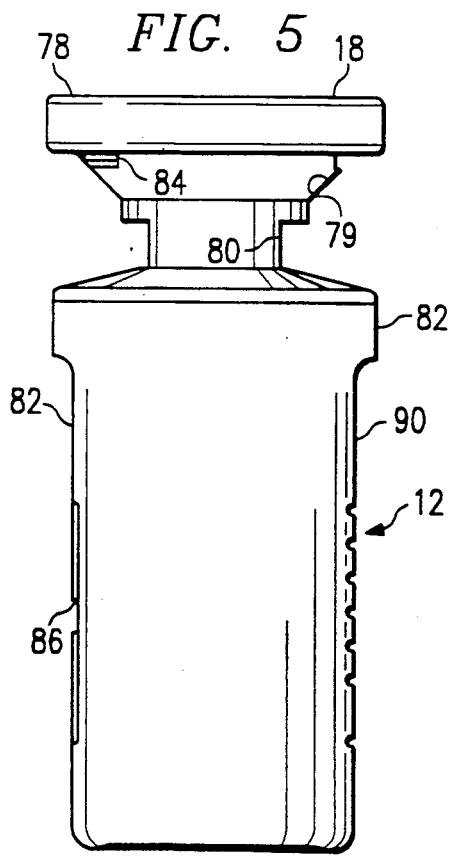

SYSTEM FOR THE DISPOSAL OF MEDICAL WASTE

TECHNICAL FIELD OF THE INVENTION

This invention relates in general to devices for disposal of medical waste, and in particular to a system wherein medical sharps and medical non-sharps are disposed.

BACKGROUND OF THE INVENTION

In medical and health-related industries, the fear of contamination from contact with bodily fluids has become a concern to all. Medical personnel now routinely wear protective garments such as masks and latex gloves whenever they may come into contact with bodily fluids. Similarly, fear of contamination requires careful handling and disposal of all items that have been in contact with bodily fluids. For example, needles, syringes, scalpels, and bandages are all collected for sanitary disposal after use. Typically, sanitary disposal includes autoclaving prior to landfilling or high temperature incineration of such items to prevent accidental contact. Since there are over 3 billion syringes (not to mention scalpels) used in the United States every year, safe and economical disposal of these contaminated items is no small concern. Additionally, there are ever increasing Federal and State regulatory requirements for the tracking of waste materials including the use of proper packaging and transportation of such materials.

The safety precautions for handling these items after use but prior to final disposal have been less than optimum. After needles and syringe bodies were used to draw blood or make an injection, they were often disposed by being tossed into a plastic garbage bag or a trash receptacle. Obviously, this was unsafe as when the garbage bag was gathered for removal or the trash can was emptied, the sharps (needles) could easily puncture anyone handling the trash.

The Environmental Protection Agency is currently operating under a test act known as the Medical Waste Tracking Act of 1988. This test act creates classifications of medical waste including sharps, such as needles, glass, scalpel blades and other discarded equipment in contact with bodily fluids and non-sharps, such as biological waste, discarded surgical materials (gauze), scalpel handles, syringe bodies and other waste deemed to be a health threat. The Act has the aim of protecting the public from exposure to waste materials. In addition, OSHA (the Occupational Safety and Health Administration) now requires sharps containers to have rigid or semirigid walls to resist puncture therethrough by sharps. Since the containers are required to be located in close proximity to all locations where sharps are used, these containers are generally quite small to prevent waste of valuable space and to facilitate ease of handling. Thus, if the sharps are deposited in one of these small containers, the container will become filled quite rapidly. Therefore, the per unit cost of a small container with puncture resistant walls can become expensive for the disposal of medical instruments, as proper disposal generally requires costly land filling of or incineration of the container along with its contents.

One example of a device that is frequently used for the disposal of sharps is known as a WALL SAFE manufactured by Bemis, Inc. The WALL SAFE resembles a mail box in that a syringe needle and attached syringe body may be laid into a horizontal chamber exposed by lifting a handle. Once the syringe is in position, the handle is dropped and the syringe is deposited into the attached container. Thus, the device requires use of both hands in a two step process which is inconvenient. The WALL SAFE is relatively small and will hold only between 85-100 syringes, thus filling quite rapidly therefore is relatively expensive. In addition, the WALL SAFE is made from polypropylene which has a tendency to soften during the autoclave process allowing some of the sharps to penetrate therethrough.

A device for the separation and disposal of medical sharps and non-sharps is disclosed in U.S. Pat. No. 4,807,344 to Kelson et al. Kelson provides an electric device capable of removing and disposing of blood sampling needles from a test tube or syringe body. Once the needle is removed, it is dropped into a container upon which the electric removing device is positioned. The electric removing device of Kelson can be expensive and inconvenient as it obviously requires an electrical outlet. Additionally the Kelson device is designed to merely remove a needle from the syringe body and does not provide for disposal of the syringe body.

Another device for the disposal of medical appliances is disclosed in U.S. Pat. No. 4,452,358 to Simpson. In one embodiment of Simpson, a syringe needle may be bent, and the entire needle and attached syringe body may then be deposited therein for disposal. In an alternative embodiment, the needle may be removed from the syringe body and deposited into the container while the syringe body may be saved. Thus, in the first embodiment, the container will become rapidly filled due to the bulky syringe bodies. In the alternative embodiment the container will not become filled as rapidly only if all the syringe bodies are saved for reuse but still presents a small container which can be rapidly filled. Thus, there is a need for a system which provides for the safe, convenient and economical disposal of medical sharps and nonsharps.

SUMMARY OF THE INVENTION

The present invention disclosed herein comprises a method and apparatus for the disposal of medical waste which greatly reduces problems associated with prior methods of disposal. The present invention allows the sanitary disposal of medical sharps and the disposal of medical nonsharps in separate containers which may be interconnected for convenience.

In accordance with one aspect of the invention, a medical disposal system comprises a nonsharps container and a disposable sharps container removably interconnected thereto. The sharps container is preferably interconnected to the nonsharps container by engagement with a holder locked into position on the nonsharps container. The device may be adapted for attachment to a vertical surface such as a wall by a bracket. An additional optional holder may also be attached to the system by any appropriate means such as by locking into position.

The nonsharps container comprises at least one disposable receptacle for receiving the nonsharps. A header associated with a supporting device is provided to support the disposable receptacle in an upright and open arrangement to allow deposit therein of nonsharps. The disposable receptacle preferably comprises flexible plastic bags having a removably covered adhesive strip for sealing of the bag prior to disposal of the bag and its contents.

The sharps container comprises a receptacle having an open end with a constricted entrance and an optional insert. The constricted entrance and optional insert provide a semitortuous path to reduce the likelihood of sharps deposited therein to spill out. When the sharps container is filled, a snap on cap is applied over the open end to seal the container for disposal.

BRIEF DESCRIPTION OF THE DRAWINGS

For a more complete understanding of the invention and for further advantages thereof, reference is now made to the following Detailed Description taken in conjunction with the accompanying Drawings in which:

FIGS. 3a-c are front, rear and side elevational views, respectively, of a sharps container;

FIG. 5 is a cross-sectional view of the sharps container of FIG. 3a along the line 5—5;

FIG. 7 is a cross-sectional view of a nonsharps container;

DETAILED DESCRIPTION OF THE INVENTION

Figure 1:
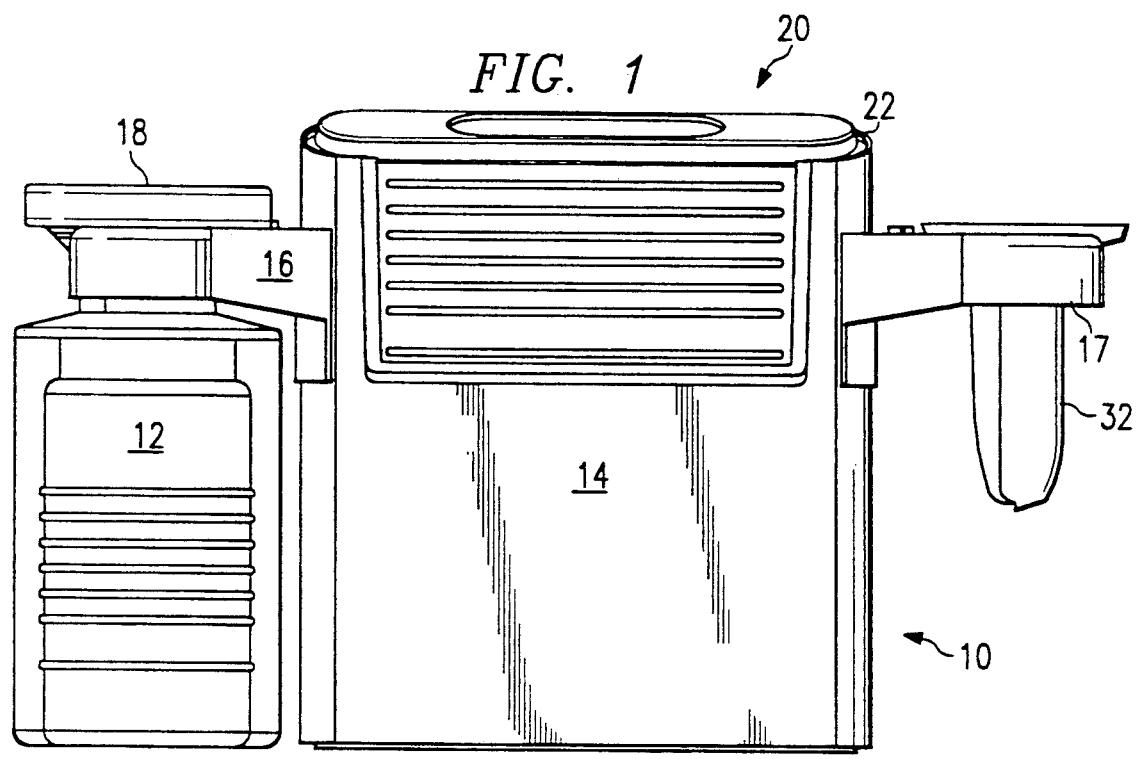
FIG. 1 is a front elevational view of a disposal system constructed in accordance with the preferred embodiment of the present invention.

In FIGS. 1-9, like items are identified by like and corresponding numerals for ease of reference. Referring first to FIG. 1, a front elevational view of a system incorporating the preferred embodiment of the present invention is generally identified by the reference numeral 10. The system 10 comprises a sharps disposal container 12, a nonsharps disposal container 14 and identical attachment holders 16 and 17.

The system 10 is designed for placement in a medical facility where it may be either free standing or attached to a vertical surface such as a wall. The system 10 is a compact device capable of safely disposing both sharp medical waste and nonsharp medical waste in one sanitary interconnected system.

The sharps disposal container 12 is removably attached to the nonsharps disposal container 14 by the attachment holder 16. Therefore, if the sharps disposal container 12 becomes full, it is merely necessary to remove the container 12 from the holder 16. An empty sharps disposal container may then be put into place on the holder 16 (or the holder 17). The sharps disposal container 12 is particularly adapted for use in conjunction with a device 32 capable of allowing safe capping, uncapping and separation of a syringe needle such as a RECAPPER offered for sale by the assignee herein, On-Gard Systems, Inc., of Denver, Colo. An open end 18 is provided on the container 12 for receiving the sharps therethrough.

The nonsharps disposal container 14 includes a header 20 removably attached thereto at an open end 22. As will be subsequently described in greater detail, the header 20 is associated with a support structure for positioning at least one disposable receptacle within the container 14. The container 14 may be provided with a bracket 38 (See FIG. 2) or other similar device for attachment to a vertical surface.

The holders 16 and 17 are removably attached to the container 14 such as by a snap lock engagement, as will be subsequently described in greater detail. The holders 16 and 17 may also be used to hold other medical devices such as the capping/uncapping safety device 32 as previously discussed above. Alternatively, a medical glove dispenser 136 (see FIG. 2) or any other medical products dispenser (such as caps, masks, gowns, etc.) may be installed on the container 14.

Figure 2:
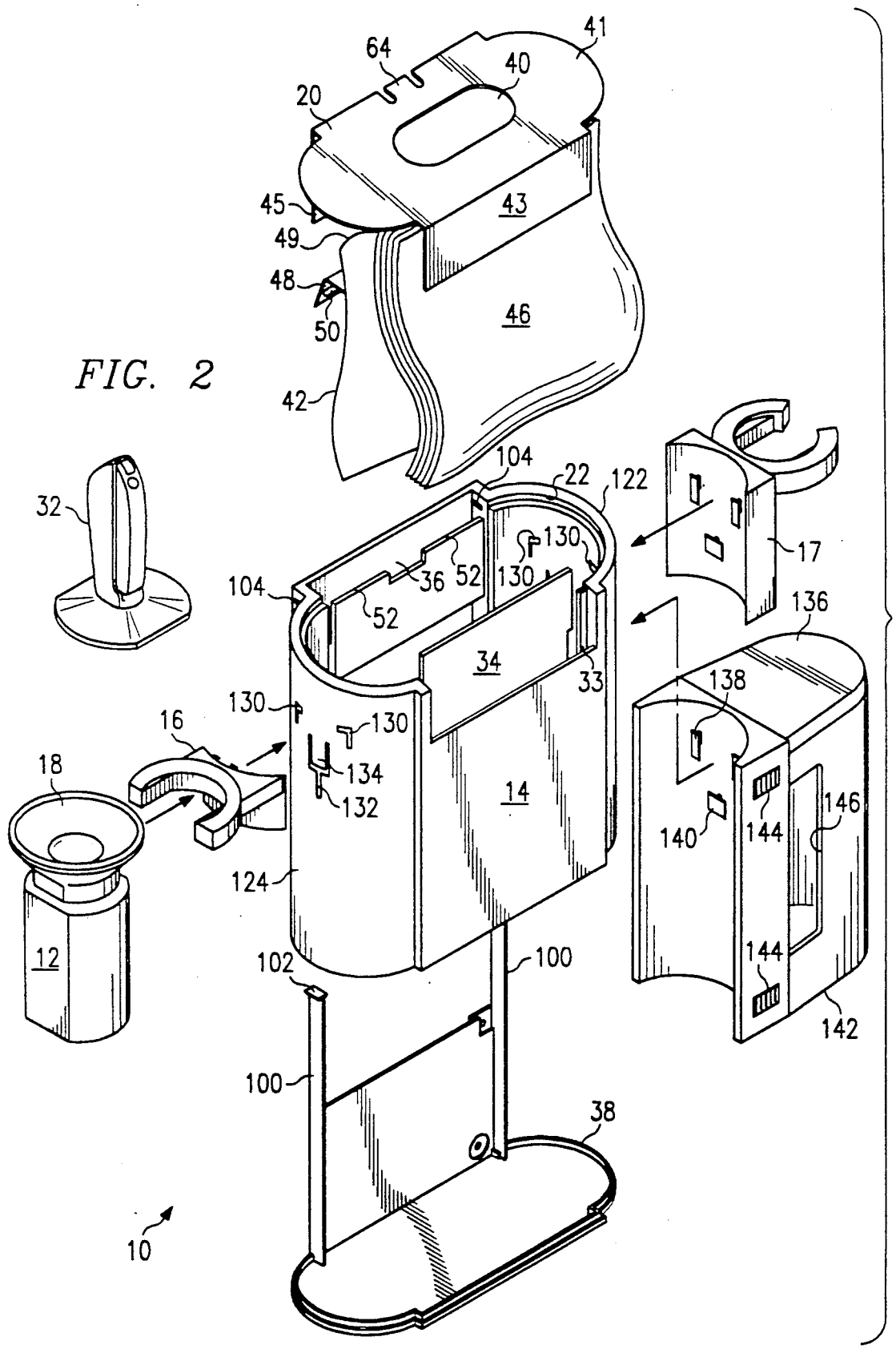
FIG. 2 is an exploded perspective view of the disposal system of FIG. 1.

Referring to FIG. 2, an exploded perspective view of the system 10 is shown. The sharps disposal container 12 may serve as a stand alone unit or may be removably attached to the nonsharps disposal container 14. Optionally, the container 12 may be attached to a vertical surface as a single unit by attaching the holder 16 or 17 to the vertical surface.

Figure 6:
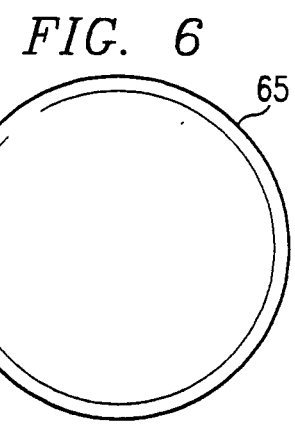
FIG. 6 is a top plan view of a cap used in conjunction with the container of FIG. 3.
Figure 6A:
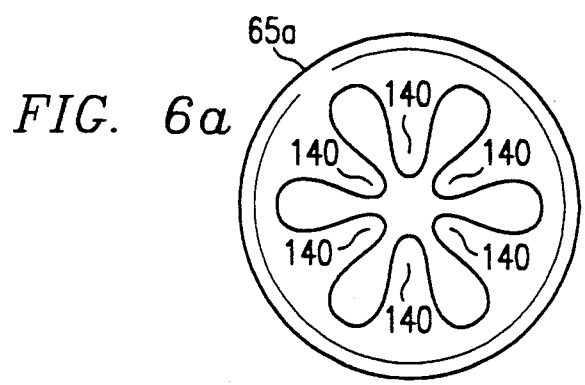
FIG. 6a is a top plan view of a snap-in insert.

The container 12 may comprise any suitable material which resists punctures therethrough by sharps. Some materials that are particularly suitable for formation of the container 12 are polycarbonate and polypropylene. In the preferred embodiment, the container 12 is formed by blow-molding translucent (to allow external inspection of the contents) polycarbonate. The container 12 receives sharps through the open end 18, which is preferably provided with a semitortuous path to limit spillage of the contents from the container 12. The tortuous path is provided by constricting the open end 18 as will be subsequently described in greater detail. Additionally, a snap-in insert 65a (see FIG. 6a) may be inserted into the open end 18 to further restrict entry therethrough. The insert 65a is formed from any suitable material such as plastic and is provided with a plurality of interference fingers 140. As previously described above, the capping/uncapping device 32 may be used in conjunction with the system 10, and the open end 18 is therefore adapted to receive and hold the device 32.

Referring to FIGS. 3a-c, 4 and 5, the container 12 is shown in greater detail. The open end 18 is formed with a wide mouth 78 (FIG. 4) that gradually tapers inwardly at 79 to a reduced diameter throat 80. The throat 80 has a length sufficient to separate the mouth 78 from the main body 82 and is then connected to the main body 82 of the container 12. A semi-tortuous path is thus formed to help reduce the likelihood of any sharps spilling from the container 12. Additionally, the throat 80 (and the separation of the mouth 78 from the main body 82 thereby) and the insert 65a (see FIG. 6a) reduces the ability of an individual to insert fingers into the container 12 thereby reducing injuries to the fingers.

The taper 79 has a plurality of locking flaps 84 which are used to secure a cap 65 or insert 65a (See FIGS. 6 and 6a) to the open end 18. By placing the cap 65 over the open end 18 and pushing downwardly, the cap 65 will be securely locked in place by locking flaps 84 to seal the container 12. The cap 65 which may comprise polycarbonate or any other appropriately durable material is die cut separately from the container 12 and fits snugly within a recess portion 86 (See FIG. 3b) until the container 12 is filled with disposable sharps. The recess 86 is preferably formed with finger notches 88 to assist in the removal of the cap 65 from the recess portion 86. As will be subsequently described in greater detail, the locking flaps 84 are also used to secure the container 12 to the holders 16 or 17.

Figure 4:
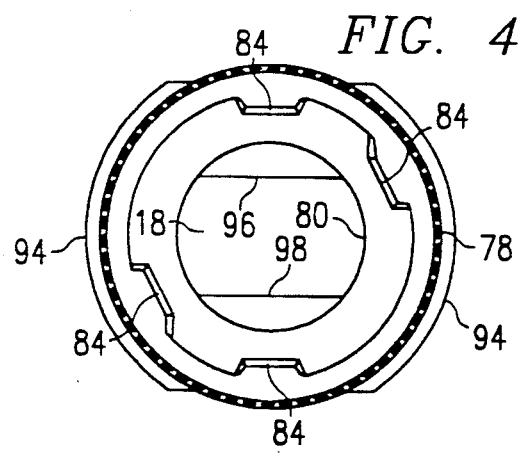
FIG. 4 is a top plan view of the sharps container of FIG. 3.

The main body 82 of the container 12 has a generally flat front wall 90 (See FIGS. 3a and 3c), a generally flat rear wall 92 (See FIGS. 3b and 3c), and generally curved sidewalls 94 (See FIG. 4). The throat 80 has correspondingly shaped walls to match the walls 90, 92 and 94 of the main body 82. Thus, the throat 80 can be seen to have oppositely facing flat walls 96 and 98 (See FIG. 4) further constricting the open end 18.

Referring to FIG. 5, a cross-sectional view of the container 12 is shown along the line 5—5 of FIG. 3a illustrating the structure of the container 12. By blow-molding translucent polycarbonate, a relatively thin-walled, yet highly puncture resistant structure may be formed in one piece. Thus, the use of a relatively expensive material such as polycarbonate may be offset by decreasing cycle time and by eliminating the need for multiple molds and the associated assembly costs.

Referring again to FIG. 2, the container 14 comprises a suitably rigid material such as, for example, ABS (acrylonitrile butadiene styrene) or high impact polystyrene, which is capable of supporting the header 20 within the open end 22. Appropriate receiving slots 33, 34 and 36 are provided for receiving the header 20, as will be subsequently described in greater detail. The container 14 may be placed on a horizontal surface or may be used in conjunction with a wall bracket 38 for attachment to a vertical surface. The bracket 38 has vertical flanges 100 with locking arms 102 (only one of which is shown) for locking engagement with slots 104 on the container 14.

The header 20 comprises a first member 41 having a feed slot 40 for allowing disposable nonsharps to pass therethrough into a disposable bag 42. The header 20 (see FIG. 7) may be a translucent thermoformed plastic and is provided with a first hinged flap 43, a second intermediate hinged flap 44, and a third hinged flap 45 for insertion into the receiving slots 33, 34 and 36, respectively. The header 20 is preferably translucent to allow external inspection of the bag 42 to know when bag 42 is in need of disposal. The disposable bag 42 is removably attached to the header 20 by any appropriate method such as by sonically bonding or stapling an edge thereof onto the flap 44. A plurality of additional disposable bags may also be similarly attached to the flap 44. It is to be understood that any appropriate arrangement may be used for receiving the header 20 within the open end 22. For example, header 20 may be provided with only first and third hinged flaps 43 and 45 with the bags 42 and 46 attached to the flap 43.

It is important to note that the slot 40 is smaller than the opening formed by the bag 42 which helps keep the disposable non-sharps from contaminating the edges of the bag 42. Thus, when the bag 42 is removed for disposal, personnel will have a reduced likelihood of coming into contact with contaminants on the bag 42.

Referring to FIG. 7, a cross-sectional view of the container 14 is illustrated with the header 20 in position thereon. The bag 42 and the plurality of additional bags 46 are attached to the flap 44 and hang freely therefrom into the container 14 until needed. To install the header 20, the first hinged flap 43 is slideably inserted into the slot 33 followed by insertion of the second intermediate flap 44 into the slot 34. Prior to inserting the third flap 45 into the slot 36, the bag 42 is opened by pulling a side 48 away from a side 49 thereof. Openings 50 (see FIGS. 2 and 8) are then positioned over tabs 52 to hang the bag 42 within the container 14 directly below the feed slot 40. The header 20 may be provided with an opening protector 70 which may comprise a cutout formed from the feed slot 40. The opening protector 70 provides a tortuous path to restrict the nonsharps within the bag 42 from spilling therefrom. A tab 64 (see FIG. 2) is provided on the first member 41 to facilitate lifting of the header 20 for removal from the container 14

Figure 8:
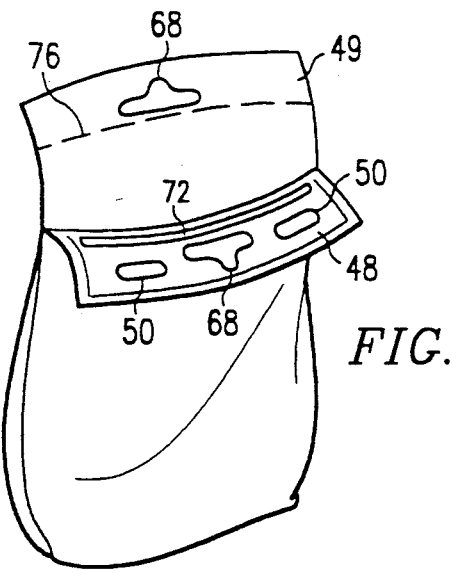
FIG. 8 is a perspective view of a disposable bag used in conjunction with the present invention.

Referring to FIG. 8, a perspective view of the disposable bag 42 is shown separated from the header 20. The bag 42 is provided with perforations 76 for easy removal from the header 20. The bag 42 is also provided with a handle 68 in at least one side thereof for ease of transport. The openings 50 are cut into the side 48 to match the receiving tabs 52 on the container 14 to allow the bag 42 to hang in an open arrangement. The bag 42 is preferably provided with an appropriate mechanism for sealing thereof to reduce the likelihood of spillage of the contents prior to disposal. For example, a removably covered adhesive strip 72 may be used to seal the bag 42. The bag 42 is appropriately color coded (red) and marked with the words "Biohazard" and symbol to indicate its contaminated contents.

In operation, the plurality of bags 46 and the bag 42 are received within the container 14 through the open end 22 by inserting the flaps 43, 44 and 45 into the receiving slots 33, 34 and 36, respectively, with the header 20 traversing the open end 22. Prior to inserting the flap 45 into the slot 36, the disposable bag 42 is opened by pulling the side 48 away from the side 49 and attaching the openings 50 to the receiving tabs 52 proximate the receiving slot 34. A nonsharp disposable item may thus be inserted through the feed slot 40 into the disposable bag 42. When the bag 42 becomes filled, it is a simple process to seal and remove the bag 42 along the perforations 76 from the flap 44 and to replace it with the next one of the plurality of bags 46.

Again referring to FIG. 2, the medical glove dispenser 136 may be locked onto the container 14 in place of the attachment holder 17. The dispenser 136 is provided with L-shaped locking tabs 138 and T-shaped locking tab 140 (identical to locking tabs 126 and 128 subsequently described herein) for locking engagement with L-shaped slots 130 and Y-shaped slot 132, respectively on the container 14. The dispenser 136 has a hinged access door 142 which may be opened by depressing locks 144. The door 142 has a cut-out 146 for dispensing medical gloves therethrough. By depressing locks 144, the access door 142 may be swung open and a supply of disposable medical gloves inserted into the dispenser 136. The door 142 may then be locked shut for the convenient dispensing of gloves therefrom through the cut-out 146.

Figure 9A:
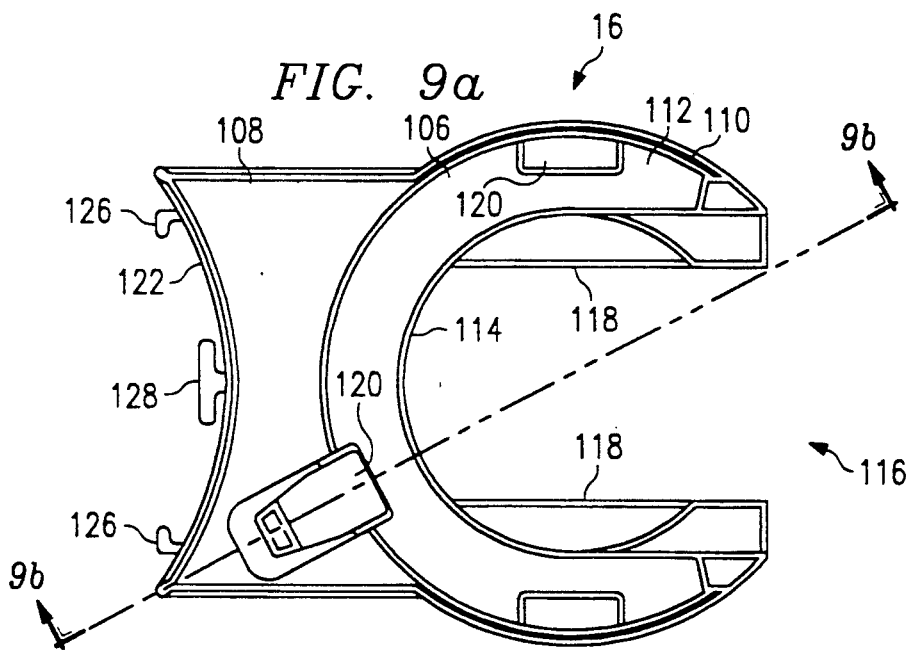
FIGS. 9a and 9b are views of a holder used in accordance with the present invention.
Figure 9B:
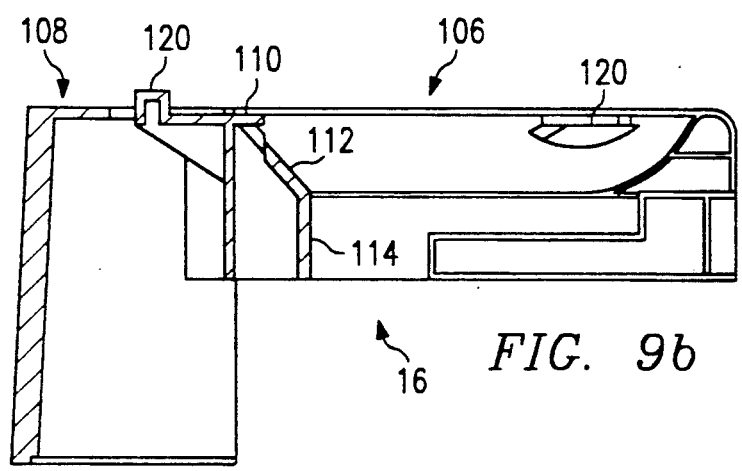

Referring to FIGS. 9a and 9b, the attachment holder 16 is shown in a top plan view and in a cross-sectional view along the line 9b—9b, respectively. Referring first to FIG. 9a, the holder 16 has a holding portion 106 and a locking/supporting portion 108. The holding portion 106 has a shape which generally matches the sharps container 12, i.e. a wide mouth 110, a taper 112 and a reduced diameter throat 114. Additionally, the holding portion 106 has an opening 116 and flat portions 118. Thus, the container 12 is received by the holding portion 106 by matching the throat 80 of the open end 18 with the opening 116 and slidingly inserting the container 12 therein. The holder 16 is provided with locking tabs 120 which mate with the locking flaps 84 (See FIGS. 3a-c and 4) of the container 12 to secure the container 12 in position.

The locking/supporting portion 108 of the holder 16 has an arcuate portion, 122 to match with a curved sidewall 122 of the container 14. L-shaped locking tabs 126 and T-shaped locking tab 128 are matingly received by L-shaped slots 130 and Y-shaped slot 132, respectively, on the sidewalls 124 of the container 14. Once the tabs 126 and 128 are inserted into the slots 130 and 132, the holder 16 is locked into place by pushing downward thereon. The Y-shaped slot is provided with a flap 134 to reduce the likelihood of accidental removal of the holder 16 from the container 14. Due to the flap 134, it would be necessary to insert some type of pointed device into the container 14 to free the tab 128 from the Y-shaped slot 132. Although not shown, it is to be understood that any other appropriate attaching arrangements, such as, for example, an "arrow head" and slot, may be used to attach the holders 16 and 17 and the dispenser 136 to the container 14.

In operation, the system 10 may be used as a system or separated into its individual components as desired. The system 10 is preferably connected to a vertical surface by matching the bracket 38 to the container 14. The container 12 is interconnected to the container 14 by the attachment holder 16 or 17, thus allowing a convenient means for disposing of sharps and non-sharps. Sharps are deposited into the disposable sharps container 12 while non-sharps are deposited into the disposable bag 42 within the container 14. The system 10 is particularly adapted for use with the capping/uncapping device 32 which may be stored in the open end 18 of the container 12 or on a separate holder 17. The container 14 may also be used as a base piece for the attachment of additional medical products such as a medical glove dispenser 136 or any other dispenser as desired.

In the convenient use of the system 10 with the capping/uncapping device 32, the safety of a person using the system is enhanced. The device 32 would be used to safely remove the syringe needle from the syringe body and then deposit the syringe needle into the container 12 without contact between the needle and the person. The detached syringe body is then simply deposited into the container 14 thus limiting further human contact with possibly contaminated waste.

Although the present invention has been described with respect to a specific preferred embodiment thereof, various changes and modifications may be suggested to one skilled in the art, and it is intended that the present invention encompass such changes and modifications as fall within the scope of the appended claims.

We claim:

1. A container for receiving medical sharps, comprising:
    a receptacle having an open end for receiving the sharps therethrough and a main body for storing the sharps therein; and
    constricting means having a portion integral to the container, and further including a plastic, snap-in insert substantially between said open end and said main body of said receptacle for restricting access to said main body and for retaining the medical sharps within said main body of said receptacle, wherein said constricting means portion comprises a wide mouth, a substantially rigid reduced diameter throat having a length connecting said mouth to said main body, and a taper from said mouth to said throat wherein a progressively constricted access to said receptacle is formed.

2. The container of claim 1, wherein said receptacle comprises:
    a rigid walled structure generally puncture resistent to the sharps.

3. The container of claim 2, wherein said rigid walled structure comprises polycarbonate.

4. The container of claim 2, wherein said rigid walled structure comprises polypropylene.

5. The container of claim 1, further including:
    a cap for enclosing the container.

6. The container of claim 1, further including means for externally interconnecting an attachment to the container.

7. The container of claim 6, wherein said attachment comprises another externally adjacent container.

8. The container of claim 1, wherein said open end is adapted to removably receive a syringe needle capping and uncapping device which fits partially within said open end.

9. The container of claim 1, wherein at least a portion of said main body is semi-transparent to permit external observation of contents of said main body.

10. The container of claim 9, wherein the container comprises polycarbonate.

11. The container of claim 9, wherein the container comprises polypropylene.

12. A container for medical nonsharps, comprising:
    a bag assembly including at least one bag and a header having a slot therein; and
    support means for supporting said bag assembly, said support means including a first member for receiving a first side portion of said one bag while said header holds a second side portion of said bag opposite said first side portion, wherein said header orients said bag relative to said support means in order to provide an opening in said bag for receiving nonsharps inserted through said slot of said header.

13. The container of claim 12, wherein said at least one bag comprises:
    a plurality of flexible plastic bags, wherein during use only one of said bags is oriented for receiving nonsharps through said slot.

14. The container of claim 13, wherein said plastic bags further comprise:
    means for sealing each of said bags.

15. The container of claim 14, wherein said means for sealing comprises:
    a removably covered adhesive strip on each of said bags.

16. The container of claim 12, wherein said bag is attached to said header by sonic bonding.

17. The container of claim 12, wherein said support means comprises:
    a rigid walled structure constructed and arranged to receive said bag assembly with said at least one bag suspended therein.

18. The container of claim 17, wherein said rigid structure comprises ABS.

19. The container of claim 17, wherein said rigid structure comprises high impact polystyrene.

20. The container of claim 12, wherein said header further comprises:
    a first member having said feed slot therethrough; and means for attaching said first member to said means for supporting.

21. The container of claim 20, wherein said means for attaching comprises:
   a first hinged flap on one edge of said first member matingly received by said support means; and
   another hinged flap on an edge of said first member opposite said first flap, wherein said other hinged flap is matingly received by said support means with said first member positioned between said first flap and said other flap.

22. The container of claim 20, wherein said feed slot is generally oval.

23. The container of claim 20, wherein said feed slot further includes an opening protector.

24. The container of claim 20, wherein said feed slot is smaller than said opening for receiving the nonsharps.

25. The container of claim 20, further including means for interconnecting at least one attachment to the container.

26. The container of claim 25, wherein said means for interconnecting comprises:
   at least one Y-shaped slot on a wall of the container for receiving a tab on said attachment, said Y-shaped slot including a flap, wherein upon insertion of said tab into said slot, said flap locks said tab therein.

27. The container of claim 26, wherein said tab comprises a T-shaped locking tab.

28. The container of claim 25, wherein said attachment comprises another container.

29. The container of claim 28, wherein said other container comprises:
   a medical glove dispenser.

30. The container of claim 12, further comprising means for mounting the container to a vertical surface.

31. A container for receiving medical sharps, comprising:
   a receptacle having an open end for receiving the sharps therethrough and a main body for storing the sharps therein;
   constricting means integral to the container and substantially between said open end and said main body of said receptacle for restricting access to said main body and for retaining the medical sharps within said main body of said receptacle, wherein said constricting means comprises a wide mouth, a substantially rigid reduced diameter throat having a length connecting said mouth to said main body, and a taper from said mouth to said throat wherein a progressively constricted access to said receptacle is formed; and
   a cap for enclosing the container, wherein said cap is stored in a sidewall of the container, said sidewall formed to define a recess for receiving said cap.

32. The container of claim 31, wherein said recess is into said sidewall such that said cap is substantially flush with said sidewall when positioned in said recess.

33. The container of claim 31, wherein said cap is shaped to be received within said constricting means.

34. The container of claim 33, wherein said constricting means further comprises:
retaining members for snapping said cap in place in said constricting means to close the container.

35. A medical disposal device, comprising:
   a nonsharps container adapted for receiving at least one disposable receptacle therein in an open orientation;
   a disposable sharps container; and
   interconnection means for attaching said sharps container to said nonsharps container, including:
   a holder removably attached to said nonsharps container, wherein a tab on the holder fits into a Y-shaped slot on a wall of the nonsharps container, said Y-shaped slot including a flap, wherein upon insertion of said tab into said slot, said flap locks said tab therein.

36. The device of claim 35, further comprising:
   a bracket for attachment of the device to a vertical surface.

37. A medical disposal device comprising:
   a nonsharps container comprising:
   (a) a plurality of disposable receptacles for receiving nonsharps;
   (b) means for supporting said receptacles;
   (c) header means associated with said means for supporting, wherein one of said receptacles is positioned on said means for supporting and said header means, in an open orientation to receive said nonsharps;
   a disposable sharps container; and
   interconnection means for attaching said sharps container to said nonsharps container.

38. The device of claim 37, wherein said plurality of disposable receptacles comprises:
   flexible plastic bags.

39. The device of claim 38, wherein said plastic bags further comprise:
   means for sealing each of said bags prior to disposal of said bags.

40. The device of claim 37, wherein said means for supporting comprises:
   a structure constructed and arranged to receive said header means with said disposable receptacles depending therefrom.

41. The device of claim 37, wherein said header means comprises:
   a first member having a feed slot therethrough; and
   means for attaching said first member to said means for supporting.

42. A header for use with a medical disposables container, comprising:
   a first member having an opening slot therethrough;
   means for attaching said member to a support integral to the container, said means for attaching comprising a first slotted portion for receiving a first flap of said first member and a second slotted portion spaced apart from said first slotted portion for receiving a second flap of said member wherein opening slot is positioned between said first and second slotted portions; and
   receiving means interconnected to said member and said support, wherein the disposables are deposited in said receiving means through said opening slot in said member.

* * * * *